(12) United States Patent
Birk et al.

(10) Patent No.: US 8,236,023 B2
(45) Date of Patent: Aug. 7, 2012

(54) APPARATUS AND METHOD FOR VOLUME ADJUSTMENT OF INTRAGASTRIC BALLOONS

(75) Inventors: Janel Birk, Oxnard, CA (US); Frederick L. Coe, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 1401 days.

(21) Appl. No.: 10/593,530

(22) PCT Filed: Mar. 18, 2004

(86) PCT No.: PCT/US2004/008236
§ 371 (c)(1),
(2), (4) Date: Sep. 18, 2006

(87) PCT Pub. No.: WO2005/094257
PCT Pub. Date: Oct. 13, 2005

(65) Prior Publication Data
US 2007/0173881 A1    Jul. 26, 2007

(51) Int. Cl.
*A61M 29/00* (2006.01)
(52) U.S. Cl. ........ 606/192; 606/151; 606/152; 606/153; 623/23.65
(58) Field of Classification Search .......... 242/371–374; 604/530–531, 525, 523; 606/191, 192, 195, 606/196, 194
See application file for complete search history.

(56) References Cited

U.S. PATENT DOCUMENTS

| | | | |
|---|---|---|---|
| 1,174,814 A | 3/1916 | Brennan et al. | |
| 1,830,947 A | 11/1931 | Klingel | |
| 1,999,683 A | 4/1935 | Borresen | |
| 2,163,048 A | 6/1939 | McKee | |
| 2,339,138 A | 1/1944 | Black | |
| 2,405,667 A | 8/1946 | Ottesen | |
| 2,438,231 A | 3/1948 | Schultz et al. | |
| 2,635,907 A | 4/1953 | Heimbuch | |

(Continued)

FOREIGN PATENT DOCUMENTS
CA    949965    6/1974
(Continued)

OTHER PUBLICATIONS

B. De Waele, et al., Endoscopic volume adjustment of intragastric balloons for intolerance; *Obesity Surgery*, 11, 2001 223-224.

(Continued)

*Primary Examiner* — Gary Jackson
*Assistant Examiner* — Katrina Stransky
(74) *Attorney, Agent, or Firm* — Debra Condino; Stephen Donovan

(57) ABSTRACT

A gastric balloon and method of adding and removing fluid therefrom are disclosed. The gastric balloon includes a shell, a receiver, and a retractable tubing housed in the receiver and extendable from the stomach of a patient to the mouth of the patient. The shell is inflated and deflated from outside the body of the patient. The method of adding or removing fluid from the implanted gastric balloon includes steps of inserting a gastroscopic tool into the stomach of a patient and grasping an end of a retractable tubing housed in a receiver of the gastric balloon. Further steps of the method include withdrawing at least a portion of the retractable tubing from the stomach and out of a patient's mouth and adding or removing fluid from the gastric balloon via the retractable tubing withdrawn from the patient.

3 Claims, 3 Drawing Sheets

U.S. PATENT DOCUMENTS

| | | | |
|---|---|---|---|
| 2,714,469 A | 8/1955 | Carlson | |
| 2,936,980 A | 5/1960 | Rapata | |
| 3,059,645 A | 10/1962 | Hasbrouck et al. | |
| 3,189,961 A | 6/1965 | Heller | |
| 3,667,081 A | 6/1972 | Burger | |
| 3,840,018 A | 10/1974 | Heifetz | |
| 3,955,834 A | 5/1976 | Ahlrot | |
| 4,053,176 A | 10/1977 | Hilbush | |
| 4,118,805 A | 10/1978 | Reimels | |
| 4,133,315 A | 1/1979 | Berman et al. | |
| 4,157,713 A | 6/1979 | Clarey | |
| 4,176,412 A | 12/1979 | Peterson | |
| 4,236,521 A | 12/1980 | Lauterjung | |
| 4,271,827 A | 6/1981 | Angelchik | |
| 4,299,012 A | 11/1981 | Oetiker | |
| 4,399,809 A | 8/1983 | Baro et al. | |
| 4,408,597 A | 10/1983 | Tenney, Jr. et al. | |
| 4,417,567 A * | 11/1983 | Trick | 600/31 |
| 4,424,208 A | 1/1984 | Wallace et al. | |
| 4,442,153 A | 4/1984 | Meltsch | |
| 4,485,805 A | 12/1984 | Foster, Jr. | |
| 4,492,004 A | 1/1985 | Oetiker | |
| 4,551,862 A | 11/1985 | Haber | |
| 4,558,699 A | 12/1985 | Bashour | |
| 4,559,699 A | 12/1985 | Owen et al. | |
| 4,582,640 A | 4/1986 | Smestad et al. | |
| 4,582,865 A | 4/1986 | Balazs et al. | |
| 4,592,339 A | 6/1986 | Kuzmak et al. | |
| 4,592,355 A | 6/1986 | Antebi | |
| 4,601,713 A | 7/1986 | Fuqua | |
| 4,671,351 A | 6/1987 | Rappe | |
| 4,693,695 A * | 9/1987 | Cheng | 446/220 |
| 4,694,827 A | 9/1987 | Weiner et al. | |
| 4,696,288 A | 9/1987 | Kuzmak et al. | |
| 4,708,140 A | 11/1987 | Baron | |
| 4,716,154 A | 12/1987 | Malson et al. | |
| 4,753,086 A | 6/1988 | Schmidt | |
| 4,760,837 A | 8/1988 | Petit | |
| 4,803,075 A | 2/1989 | Wallace et al. | |
| 4,881,939 A | 11/1989 | Newman | |
| 4,883,467 A | 11/1989 | Franetzki et al. | |
| 4,886,787 A | 12/1989 | De Belder et al. | |
| 4,896,787 A | 1/1990 | Delamour et al. | |
| 4,915,690 A | 4/1990 | Cone et al. | |
| 4,925,446 A * | 5/1990 | Garay et al. | 604/103.02 |
| 4,944,659 A | 7/1990 | Labbe et al. | |
| 4,958,791 A | 9/1990 | Nakamura | |
| 4,969,899 A * | 11/1990 | Cox, Jr. | 623/8 |
| 4,994,019 A | 2/1991 | Fernandez et al. | |
| 5,045,060 A | 9/1991 | Melsky et al. | |
| 5,074,868 A | 12/1991 | Kuzmak | |
| 5,084,061 A * | 1/1992 | Gau et al. | 606/195 |
| 5,091,171 A | 2/1992 | Yu et al. | |
| 5,120,313 A | 6/1992 | Elftman | |
| 5,143,724 A | 9/1992 | Leshchiner et al. | |
| 5,152,770 A | 10/1992 | Bengmark et al. | |
| 5,160,338 A | 11/1992 | Vincent | |
| 5,188,609 A | 2/1993 | Bayless et al. | |
| 5,224,494 A | 7/1993 | Enhorning | |
| 5,226,429 A | 7/1993 | Kuzmak | |
| 5,246,456 A | 9/1993 | Wilkinson | |
| 5,246,698 A | 9/1993 | Leshchiner et al. | |
| 5,259,399 A | 11/1993 | Brown | |
| 5,326,349 A | 7/1994 | Baraff | |
| 5,356,883 A | 10/1994 | Kuo et al. | |
| 5,360,445 A | 11/1994 | Goldowsky | |
| 5,391,156 A | 2/1995 | Hildwein et al. | |
| 5,399,351 A | 3/1995 | Leshchiner et al. | |
| 5,449,363 A | 9/1995 | Brust et al. | |
| 5,449,368 A | 9/1995 | Kuzmak | |
| 5,509,888 A | 4/1996 | Miller | |
| 5,531,716 A | 7/1996 | Luzio et al. | |
| 5,535,752 A | 7/1996 | Halperin et al. | |
| 5,554,113 A | 9/1996 | Novak et al. | |
| 5,562,714 A | 10/1996 | Grevious | |
| 5,601,604 A | 2/1997 | Vincent | |
| 5,607,418 A | 3/1997 | Arzbaecher | |
| 5,633,001 A | 5/1997 | Agerup | |
| 5,653,718 A | 8/1997 | Yoon | |
| 5,658,298 A | 8/1997 | Vincent et al. | |
| 5,676,162 A | 10/1997 | Larson, Jr. et al. | |
| 5,695,504 A | 12/1997 | Gifford, III et al. | |
| 5,704,893 A | 1/1998 | Timm | |
| 5,713,911 A | 2/1998 | Racenet et al. | |
| 5,748,200 A | 5/1998 | Funahashi | |
| 5,766,232 A | 6/1998 | Grevious et al. | |
| 5,769,877 A | 6/1998 | Barreras, Sr. | |
| 5,785,295 A | 7/1998 | Tsai | |
| 5,817,113 A | 10/1998 | Gifford, III et al. | |
| 5,827,529 A | 10/1998 | Ono et al. | |
| 5,833,698 A | 11/1998 | Hinchliffe et al. | |
| 5,861,014 A | 1/1999 | Familoni | |
| RE36,176 E | 3/1999 | Kuzmak | |
| 5,886,042 A | 3/1999 | Yu et al. | |
| 5,904,697 A | 5/1999 | Gifford, III et al. | |
| 5,910,149 A | 6/1999 | Kuzmak | |
| 5,928,195 A | 7/1999 | Malamud et al. | |
| 5,938,669 A | 8/1999 | Klaiber et al. | |
| 5,944,696 A | 8/1999 | Bayless et al. | |
| 5,944,751 A | 8/1999 | Laub | |
| 5,993,473 A | 11/1999 | Chan et al. | |
| 6,013,679 A | 1/2000 | Kuo et al. | |
| 6,024,340 A | 2/2000 | Lazarus et al. | |
| 6,024,704 A | 2/2000 | Meador et al. | |
| 6,048,309 A | 4/2000 | Flom et al. | |
| 6,067,991 A | 5/2000 | Forsell | |
| 6,074,341 A | 6/2000 | Anderson et al. | |
| 6,074,378 A * | 6/2000 | Mouri et al. | 604/523 |
| 6,083,249 A | 7/2000 | Familoni | |
| 6,090,131 A | 7/2000 | Daley | |
| 6,102,678 A | 8/2000 | Peclat | |
| 6,102,922 A | 8/2000 | Jakobsson et al. | |
| 6,171,321 B1 | 1/2001 | Gifford, III et al. | |
| 6,193,734 B1 | 2/2001 | Bolduc et al. | |
| 6,203,523 B1 | 3/2001 | Haller et al. | |
| 6,210,345 B1 | 4/2001 | Van Brunt | |
| 6,210,347 B1 | 4/2001 | Forsell | |
| 6,221,024 B1 | 4/2001 | Miesel | |
| 6,224,857 B1 | 5/2001 | Romeo et al. | |
| 6,306,088 B1 | 10/2001 | Krausman et al. | |
| 6,327,503 B1 | 12/2001 | Familoni | |
| 6,371,965 B2 | 4/2002 | Gifford, III et al. | |
| 6,387,105 B1 | 5/2002 | Gifford, III et al. | |
| 6,417,750 B1 | 7/2002 | Shon | |
| 6,419,696 B1 | 7/2002 | Ortiz et al. | |
| 6,432,040 B1 | 8/2002 | Meah | |
| 6,439,539 B1 | 8/2002 | Powell | |
| 6,443,957 B1 | 9/2002 | Addis | |
| 6,443,965 B1 | 9/2002 | Gifford, III et al. | |
| 6,450,173 B1 | 9/2002 | Forsell | |
| 6,450,946 B1 | 9/2002 | Forsell | |
| 6,451,034 B1 | 9/2002 | Gifford, III et al. | |
| 6,453,907 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,454,785 B2 | 9/2002 | De Hoyos Garza | |
| 6,457,801 B1 | 10/2002 | Fish et al. | |
| 6,460,543 B1 | 10/2002 | Forsell | |
| 6,461,293 B1 | 10/2002 | Forsell | |
| 6,463,935 B1 | 10/2002 | Forsell | |
| 6,464,628 B1 | 10/2002 | Forsell | |
| 6,470,892 B1 | 10/2002 | Forsell | |
| 6,474,584 B2 * | 11/2002 | Ekich | 242/371 |
| 6,475,136 B1 | 11/2002 | Forsell | |
| 6,485,496 B1 | 11/2002 | Suyker et al. | |
| 6,491,704 B2 | 12/2002 | Gifford, III et al. | |
| 6,491,705 B2 | 12/2002 | Gifford, III et al. | |
| 6,511,490 B2 | 1/2003 | Robert | |
| 6,517,556 B1 | 2/2003 | Monassevitch | |
| 6,527,701 B1 | 3/2003 | Sayet et al. | |
| 6,547,801 B1 | 4/2003 | Dargent et al. | |
| 6,565,582 B2 | 5/2003 | Gifford, III et al. | |
| 6,579,301 B1 | 6/2003 | Bales et al. | |
| 6,601,604 B1 | 8/2003 | Cooper | |
| 6,615,084 B1 | 9/2003 | Cigaina | |
| 6,632,239 B2 | 10/2003 | Snyder et al. | |

| | | | | | |
|---|---|---|---|---|---|
| 6,646,628 B2 | 11/2003 | Shirochi et al. | 7,794,386 B2 | 9/2010 | Brooks |
| 6,676,674 B1 | 1/2004 | Dudai | 7,811,298 B2 | 10/2010 | Birk |
| 6,685,668 B1 | 2/2004 | Cho et al. | 7,824,422 B2 | 11/2010 | Benchetrit |
| 6,691,047 B1 | 2/2004 | Fredericks | 7,828,813 B2 | 11/2010 | Mouton |
| 6,715,731 B1 | 4/2004 | Post et al. | 7,832,407 B2 | 11/2010 | Gertner |
| 6,729,600 B2 | 5/2004 | Mattes et al. | 7,841,978 B2 | 11/2010 | Gertner |
| 6,754,527 B1 | 6/2004 | Stroebel et al. | 7,844,342 B2 | 11/2010 | Dlugos, Jr. et al. |
| 6,811,136 B2 | 11/2004 | Eberhardt et al. | 7,862,502 B2 | 1/2011 | Pool et al. |
| 6,820,651 B2 | 11/2004 | Seuret et al. | 7,879,068 B2 | 2/2011 | Dlugos et al. |
| 6,834,201 B2 | 12/2004 | Gillies et al. | 7,951,067 B2 | 5/2011 | Byrum et al. |
| 6,871,090 B1 | 3/2005 | He et al. | 2001/0011543 A1 | 8/2001 | Forsell |
| 6,889,086 B2 | 5/2005 | Mass et al. | 2002/0072780 A1 | 6/2002 | Foley |
| 6,916,326 B2 | 7/2005 | Benchetrit | 2002/0091395 A1 | 7/2002 | Gabbay |
| 6,940,467 B2 | 9/2005 | Fisher et al. | 2002/0095181 A1 | 7/2002 | Beyar |
| 6,966,875 B1 | 11/2005 | Longobardi | 2002/0098097 A1 | 7/2002 | Singh |
| 7,017,583 B2 | 3/2006 | Forsell | 2002/0139208 A1 | 10/2002 | Yatskov |
| 7,021,147 B1 | 4/2006 | Subramanian et al. | 2002/0183765 A1* | 12/2002 | Adams ................... 606/139 |
| 7,037,344 B2 | 5/2006 | Kagan et al. | 2002/0198548 A1 | 12/2002 | Robert |
| 7,040,349 B2 | 5/2006 | Moler et al. | 2003/0014003 A1 | 1/2003 | Gertner |
| 7,054,690 B2 | 5/2006 | Imran | 2003/0019498 A1 | 1/2003 | Forsell |
| 7,058,434 B2 | 6/2006 | Wang et al. | 2003/0045775 A1 | 3/2003 | Forsell |
| 7,060,080 B2 | 6/2006 | Bachmann | 2003/0045902 A1 | 3/2003 | Weadock |
| 7,066,486 B2 | 6/2006 | Lee | 2003/0060873 A1 | 3/2003 | Gertner et al. |
| 7,118,526 B2 | 10/2006 | Egle | 2003/0066536 A1 | 4/2003 | Forsell |
| 7,119,062 B1 | 10/2006 | Alvis et al. | 2003/0073880 A1 | 4/2003 | Polsky et al. |
| 7,128,750 B1 | 10/2006 | Stergiopulos | 2003/0093157 A1 | 5/2003 | Caseres et al. |
| 7,144,400 B2 | 12/2006 | Byrum et al. | 2003/0100910 A1 | 5/2003 | Gifford, III et al. |
| 7,172,607 B2 | 2/2007 | Hofle et al. | 2003/0120288 A1 | 6/2003 | Benchetrit |
| 7,177,693 B2 | 2/2007 | Starkebsum | 2003/0148995 A1 | 8/2003 | Piron et al. |
| 7,191,007 B2 | 3/2007 | Desai et al. | 2003/0158564 A1 | 8/2003 | Benchetrit |
| 7,204,821 B1 | 4/2007 | Clare et al. | 2003/0158569 A1* | 8/2003 | Wazne ................... 606/191 |
| 7,223,239 B2 | 5/2007 | Schulze et al. | 2003/0181890 A1 | 9/2003 | Schulze et al. |
| 7,238,191 B2 | 7/2007 | Bachmann | 2003/0181917 A1 | 9/2003 | Gertner |
| 7,240,607 B2 | 7/2007 | Fish | 2003/0208212 A1 | 11/2003 | Cigaina |
| 7,255,675 B2 | 8/2007 | Gertner et al. | 2004/0044332 A1 | 3/2004 | Stergiopulos |
| 7,263,405 B2 | 8/2007 | Boveja et al. | 2004/0049209 A1 | 3/2004 | Benchetrit |
| 7,282,023 B2 | 10/2007 | Frering | 2004/0059393 A1 | 3/2004 | Policker et al. |
| 7,288,064 B2 | 10/2007 | Boustani et al. | 2004/0068847 A1 | 4/2004 | Belisle et al. |
| 7,297,103 B2 | 11/2007 | Jarsaillon et al. | 2004/0133219 A1 | 7/2004 | Forsell |
| 7,299,082 B2 | 11/2007 | Feldman et al. | 2004/0147816 A1 | 7/2004 | Policker et al. |
| 7,311,716 B2 | 12/2007 | Byrun | 2004/0148034 A1 | 7/2004 | Kagan et al. |
| 7,311,717 B2 | 12/2007 | Egle | 2004/0153106 A1 | 8/2004 | Dudai |
| 7,314,443 B2 | 1/2008 | Jordan et al. | 2004/0162595 A1 | 8/2004 | Foley |
| 7,314,636 B2 | 1/2008 | Caseres et al. | 2004/0215159 A1 | 10/2004 | Forsell |
| 7,338,433 B2 | 3/2008 | Coe | 2004/0230137 A1 | 11/2004 | Mouton |
| 7,340,306 B2 | 3/2008 | Barrett et al. | 2004/0254536 A1 | 12/2004 | Conlon et al. |
| 7,351,198 B2 | 4/2008 | Byrum et al. | 2004/0254537 A1 | 12/2004 | Conlon et al. |
| 7,351,240 B2 | 4/2008 | Hassler, Jr. et al. | 2004/0260319 A1 | 12/2004 | Egle |
| 7,364,542 B2 | 4/2008 | Jambor et al. | 2004/0267288 A1 | 12/2004 | Byrum et al. |
| 7,367,340 B2 | 5/2008 | Nelson et al. | 2004/0267291 A1 | 12/2004 | Byrum et al. |
| 7,367,937 B2 | 5/2008 | Jambor et al. | 2004/0267292 A1 | 12/2004 | Byrum et al. |
| 7,374,565 B2 | 5/2008 | Hassler, Jr. et al. | 2004/0267293 A1 | 12/2004 | Byrum et al. |
| 7,390,294 B2 | 6/2008 | Hassler, Jr. | 2004/0267377 A1 | 12/2004 | Egle |
| 7,396,353 B2 | 7/2008 | Lorenzen et al. | 2005/0002984 A1 | 1/2005 | Byrum et al. |
| 7,416,528 B2 | 8/2008 | Crawford et al. | 2005/0038484 A1 | 2/2005 | Knudson et al. |
| 7,457,668 B2 | 11/2008 | Cancel et al. | 2005/0038498 A1 | 2/2005 | Dubrow et al. |
| 7,481,763 B2 | 1/2009 | Hassler, Jr. et al. | 2005/0055039 A1 | 3/2005 | Burnett et al. |
| 7,500,944 B2 | 3/2009 | Byrum et al. | 2005/0070934 A1 | 3/2005 | Tanaka et al. |
| 7,502,649 B2 | 3/2009 | Ben-Haim et al. | 2005/0070937 A1 | 3/2005 | Jambor et al. |
| 7,530,943 B2 | 5/2009 | Lechner | 2005/0100779 A1 | 5/2005 | Gertner |
| 7,594,885 B2 | 9/2009 | Byrum | 2005/0104457 A1 | 5/2005 | Jordan et al. |
| 7,599,743 B2 | 10/2009 | Hassler, Jr. et al. | 2005/0119672 A1 | 6/2005 | Benchetrit |
| 7,599,744 B2 | 10/2009 | Giordano et al. | 2005/0119674 A1 | 6/2005 | Gingras |
| 7,601,162 B2 | 10/2009 | Hassler, Jr. et al. | 2005/0131383 A1 | 6/2005 | Chen et al. |
| 7,615,001 B2 | 11/2009 | Jambor et al. | 2005/0131485 A1 | 6/2005 | Krundson et al. |
| 7,618,365 B2 | 11/2009 | Jambor et al. | 2005/0136122 A1 | 6/2005 | Sadozai et al. |
| 7,658,196 B2 | 2/2010 | Ferreri et al. | 2005/0142152 A1 | 6/2005 | Leshchiner et al. |
| 7,670,279 B2 | 3/2010 | Gertner | 2005/0143765 A1 | 6/2005 | Bachmann et al. |
| 7,699,770 B2 | 4/2010 | Hassler, Jr. et al. | 2005/0143766 A1 | 6/2005 | Bachmann et al. |
| 7,712,470 B2 | 5/2010 | Gertner | 2005/0154274 A1 | 7/2005 | Jarsaillon et al. |
| 7,727,141 B2 | 6/2010 | Hassler, Jr. et al. | 2005/0171568 A1* | 8/2005 | Duffy ................... 606/191 |
| 7,741,476 B2 | 6/2010 | Lebreton | 2005/0183730 A1 | 8/2005 | Byrum |
| 7,758,493 B2 | 7/2010 | Gingras | 2005/0192531 A1 | 9/2005 | Birk |
| 7,763,039 B2 | 7/2010 | Ortiz et al. | 2005/0192601 A1 | 9/2005 | Demarais |
| 7,766,815 B2 | 8/2010 | Ortiz | 2005/0192629 A1 | 9/2005 | Saadat et al. |
| 7,771,439 B2 | 8/2010 | Griffiths | 2005/0216042 A1 | 9/2005 | Gertner |
| 7,775,215 B2 | 8/2010 | Hassler, Jr. et al. | 2005/0226936 A1 | 10/2005 | Agerup |
| 7,775,966 B2 | 8/2010 | Dlugos et al. | 2005/0228415 A1 | 10/2005 | Gertner |
| 7,775,967 B2 | 8/2010 | Gertner | 2005/0228504 A1 | 10/2005 | Demarais |

| Publication No. | Date | Inventor |
|---|---|---|
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neil |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |

| | | | |
|---|---|---|---|
| 2010/0168508 A1 | 7/2010 | Gertner | |
| 2010/0185049 A1 | 7/2010 | Birk et al. | |
| 2010/0191265 A1 | 7/2010 | Lau et al. | |
| 2010/0191271 A1 | 7/2010 | Lau et al. | |
| 2010/0204647 A1 | 8/2010 | Gertner | |
| 2010/0204723 A1 | 8/2010 | Gertner | |
| 2010/0226988 A1 | 9/2010 | Lebreton | |
| 2010/0228080 A1 | 9/2010 | Tavori et al. | |
| 2010/0234682 A1 | 9/2010 | Gertner | |
| 2010/0249803 A1 | 9/2010 | Griffiths | |
| 2010/0280310 A1 | 11/2010 | Raven | |
| 2010/0305397 A1 | 12/2010 | Birk et al. | |
| 2010/0312147 A1 | 12/2010 | Gertner | |
| 2010/0324358 A1 | 12/2010 | Birk et al. | |
| 2010/0324359 A1 | 12/2010 | Birk | |
| 2011/0201874 A1 | 8/2011 | Birk et al. | |

FOREIGN PATENT DOCUMENTS

| | | |
|---|---|---|
| CN | 1250382 | 4/2000 |
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2095796 | 9/2009 |
| EP | 2095798 | 9/2009 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 A | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO90/036947 A | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO01/68007 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

B. De Waele, et al., Intragastric balloons for preoperative weight reduction; *Obesity Surgery*, 10, 58-60.

C.H. Wahlen, et al., The BioEnterics Intragastric Balloon (BIB): how to use it; *Obesity Surgery* 11. 2001; 524-527.

E. Mathus-Vliegen, et al., Intragastric balloons for morbid obesity: results, patient tolerance and balloon life span; *Br. J. Surg.*, vol. 77, No. 1 Jan. 1990; 76-79.

E. Mathus-Vliegen, Treating morbid and supermorbid obesity; *International Journal of Gastroenterology*, 5, 1, 2000; 9-12.

E. Totte, et al., Weight reduction by means of intragastric device: Experience with the BioEnterics Intragastric Balloon; *Obesity Surgery* 11; 519-523.

G. Galloro, et al., Preliminary endoscopic technical report of a new silicone intragastric balloon in the treatment of morbid obesity; *Obesity Surgery*, 9, 1999, 68-71.

R. Weiner, et al., Preparation of extremely obese patients for laparoscopic gastric banding by gastric balloon therapy; *Obesity Surgery*, 9, 261-264.

R.M. Hodson; et al., Management of obesity with the new intragastric balloon; *Obesity Surgery*, 11, 2001 327-329.

S.B. Doldi, et al., Intragastric balloon in obese patients; *Obesity Surgery*, 10, 578-581.

S.B. Doldi, et al., Intragastric balloon: another option for treatment of obesity and morbid obesity; *Hepato-gastroenterology*, Jan.-Feb. 51(55), 2004, 294-207.

S.B. Doldi, et al., Treatment of morbid obesity with intragastric balloon in association with diet; *Obesity Surgery*, 10, 2000, 583-587.

BioEnterics Corporation, an Inamed Company, BioEnterics Intragastric Balloon; Directions for Use published document, P/N 94200 Rev: B, pp. 1-56.

"Innovative medical devices and implants"; LGSP medical futures, p. 5.

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

Adrian et al.; "Mechanism of Pancreatic Polypeptide Release in Man." The Lancet; pp. 161-163; Jan. 22, 1977.

Anson; "Shape Memory Alloys—Medical Applications," Source: Materials World, vol. 7, No. 12, pp. 745-747, Dec. 1999.

Asakawa et al; "Antagonism of Ghrelin Receptor Reduces Food Intake and Body Weight Gain in Mice"; Gut.; V.52; pp. 947-952; 2003.

Baggio et al. "Biology of Incretins: GLP-1 and GIP"; Gastroenrology; V. 132; pp. 2131-2157; 2007.

Ballantyne; "Peptide YY(1-36) and Peptide YY(3-36): Part I. Distribution, Release, and Actions"; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; "Physiology"; V. 5; pp. 55-57, 210, 428, 540, 554, 579, 584, 591; 2004.

BioEnterics Lap-Band Adjustable Gastric Banding System, Inamed Health, pub., pp. 1-115; Aug. 28, 2003.

Boulant et al.; "Cholecystokinin in Transient Lower Oesophageal Sphincter Relaxation Due to Gastric Distension in Humans"; Gut.; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Brown et al; "Symmetrical Pouch Dilation After Laparoscopic Adjustable Gastric Banding: Incidence and Management"; Obesity Surgery; V. 18, pp. 1104-1108; 2008.

Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Chaptini et al.; "Neuroendocrine Regulation of Food Intake"; Current Opinion in Gastroenterology; V. 24; pp. 223-229; 2008.

Chaudhri; "Can Gut Hormones Control Appetite and Prevent Obesity?" Diabetes Care; V. 31; Supp 2; pp. S284-S289; Feb. 2008.

Cohen et al.; "Oxyntomodulin Suppresses Appetite and Reduces Food Intake in Humans"; J. Clin. Endocrinol. Metab.; V. 88; No. 10; pp. 4696-4701; 2003.

Corno et al.; "A new implantable device for telemetric control of pulmonary blood flow"; New ideas; received Apr. 24, 2004; received in revised form Jul. 12, 2002; 10 pages.

Corno et al.; "FlowWatchTM in clipped and inclipped position"; Interact Cardio Vase Thorac Surg 2002; 1:46-49; Copyright @ 2002 The European Asociation for Cardio-thoracic Surgery; 1 page.

Cummings et al.; "Plasma Ghrelin Levels After Diet-Induced Weight Loss or Gastric Bypass Sugery"; N. Engl J. Med; V. 346, No. 21; pp. 1623-1630; May 23, 2002.

Cummings; "Gastrointestinal Regulation of Foot Intake"; The Food Journal of Clinical Investigation; V. 117, N. 1; pp. 13-23; Jan. 2007.

Dakin et al.; "Oxyntomodulin Inhibits Food Intake in the Rat"; Endocrinology; V. 142; No. 10; pp. 4244-4250; 2001.

Dakin et al.; "Peripheral Oxyntomodulin Reduces Food Intake and Body Weight gain in Rats"; Endocrinology; V. 145; No. 6; pp. 2687-2695; Jun. 2004.

Davison; "Activation of Vagal-Gastric Mechanoreceptors by Cholecystokinin"; Proc. West. Pharmocol. Soc.; V. 29; pp. 363-366; 1986.

Desai et al.; "Molecular Weight of Heparin Using 13C Nuclear Magnetic Resonance Spectroscopy" Journal of Pharmaceutical Science, V. 84, I 2; 1995, Abstract only.

Dixon et al.; "Pregnancy After Lap-Band Surgery: Management of the Band to Achieve Healthy Weight Outcomes"; Obesity Surgery; V. 11, pp. 59-65; 2001.

Ekblad et al.; "Distribution of Pancreatic Peptide and Peptide-YY"; Peptides; V. 23; pp. 251-261; 2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

GinShiCel MH Hydroxy Propyl Methyl Cellulose, Web Page http://www.ginshicel.cn/MHPC.html, Nov. 12, 2008.

Girard; "The incretins: From the concept to their use in the treatment of type 2 diabetes. Part A: Incretins: Concept and physiological functions"; Diabetes and Metabolism; V. 34; pp. 550-559; 2008.

Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.

Grise et al.; "Peptide YY Inhibits Growth of Human Breast Cancer in Vitro and in Vivo"; Journal of Surgical Research; V. 82; pp. 151-155; 1999.

Grundy; "Signaling the State of the Digestive Tract"; Autonomic Neuroscience: Basic and Clinical; V. 125; pp. 76-80; 2006.

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al.; "Gut hormones and appetite control." Oral Diseases; V. 15; pp. 18-26; 2009.

Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.

Helioscopie Product Insert for Heliogast, 1 page; Jun. 2009.

Holzer; "Gastrointestinal Afferents as Targets of Novel Drugs for the Treatment of Functional Bowel Disorders and Visceral Pain"; European Journal of Pharmacology; V. 429; pp. 177-193; 2001.

Houpt; "Gastrointestinal Factors in Hunger and Satiety." Neuroscience and Behavioral Reviews; V. 6; pp. 145-164; 1982.

Jones; "Molecular, pharmacological, and clinical aspects of liraglutide, a oncedaily human GLP-1 analogue"; Molecular and Cellular Endocrinology; V. 297; pp. 137-140; 2009.

Kerem et al.; "Exogenous Ghrelin Enhances Endocrine and Exocrine Regeneration in Pancreatectomized Rats"; J Gastrointest Surg.; V.13; pp. 775-783, 2009.

Kesty et al.; "Hormone-based therapies in the regulation of fuel metabolism and body weight"; Expert Opin. Biol. Ther.; V. 8; No. 11; pp. 1733-1747; 2008.

Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.

Kojima et al.; "A role for pancreatic polypeptide in feeding and body weight regulation." Peptides; V. 28; pp. 459-463; 2007.

Kulicke et al. "Visco-Elastic Propeerties of Sodium Hyaluronate Solutions," American Institute of Physics; pp. 585-587; 2008.

Lap-Band AP System Adjustable Gastric Banding System With OmniformTM Design: Directions for Use (DFU); Allergan, 16 pages; 2009.

Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.

Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.

Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Neary et al.; "Peptide YY(3-36) and Glucagon-Like Peptide-$1_{(7-36)}$ Inhibit Food Intake Additively"; Endocrinology; V.146; pp. 5120-5127; 2005.

Padidela et al.; "Elevated basal and post-feed glucagon-like petide 1 (GLP-1) concentrations in the neonatel period"; European Journal of Endocrinology; v. 160; pp. 53-58; 2009.

Patient Management After Lap-Band Placement; 5 pages, No Date.

Potier et al.; "Protein, amino acids, and the control of food intake"; Current Opinion in Clinical Nutrition and Metabolic Care; V. 12; pp. 54-58; 2009.

Qjan et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Shi et al.; "Sexually Dimorphic Responses to Fat Loss After Caloric Restriction or Surgical Lipectomy"; Am. J. Physiol. Endocrinol. Metab.; V. 293; E316-E326; 2007.

Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.

Small et al.; "Gut hormones and the control of appetite"; TRENDS in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

The Lap-Band Device & How it Works; http://lapband.com/en/learn_about-lapband/device_how_it_works/; 2 pages.

Tolhurst et al.; "Nutritional regulation of glucagon-like peptide1 secretion"; J. Physiol.; V. 587, No. 1; pp. 27-32; 2009.

Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wang et al.; "Plasma Ghrelin Modulation in Gastric Band Operation and Sleeve Gastrectomy"; Obes. Surg.; pp. 357-362; 2008.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

APPARATUS AND METHOD FOR VOLUME ADJUSTMENT OF INTRAGASTRIC BALLOONS

BACKGROUND OF THE INVENTION

1. Field of the Invention

The present invention is directed to adjustment devices and methods that enable inflatable intragastric balloons used for the treatment of obesity to be filled, and in particular devices and methods that enable the intragastric balloon to be filled, adjusted or deflated from outside of the stomach through non-surgical means while the device itself is in the stomach.

2. Description of the Related Art

Intragastric balloons are well known in art as a means for treating obesity. One such inflatable intragastric balloon is described in U.S. Pat. No. 5,084,061, and is commercially available as the BioEnterics Intragastric Balloon System (sold under the trademark BIB®). These devices are designed to provide therapy for moderately obese individuals who need to shed pounds in preparation for surgery, or as part of a dietary or behavioral modification program.

The BIB System, for example, consists of a silicone elastomer gastric balloon that is inserted into the stomach and filled with fluid. Commercially available gastric balloons are filled with saline solution or air. The gastric balloon functions by filling the stomach and enhancing appetite control. Placement of the gastric balloon is non-surgical, usually requiring no more than 20-30 minutes. The procedure is performed endoscopically in an outpatient setting, typically using local anesthesia and sedation. Placement is temporary, and gastric balloons are typically removed after six months.

Most gastric balloons utilized for this purpose are placed in the stomach in an empty or deflated state and thereafter filled (fully or partially) with a suitable fluid through a filler tube. The filler tube can be either removable or permanently attached to the balloon. The removable filler tube is typically attached prior to initial placement of the gastric balloon and then removed after inflation. The balloon occupies space in the stomach, thereby leaving less room available for food and creating a feeling of satiety for the obese person. Clinical results with these devices show that for many obese patients, the intragastric balloons significantly help to control appetite and accomplish weight loss.

Among the intragastric balloons described in the prior art, one type remains connected to a filler tube during the entire time period while the balloon is in the stomach. The balloon is introduced into the patient's stomach and a connected tube is extended through the nostril. Such an intragastric balloon is described, for example, in U.S. Pat. No. 4,133,315.

Another type of intragastric balloon of the prior art is placed into the stomach with the assistance of an appropriate plastic tube and usually a stylette. The balloon is filled with saline, whereafter the tube and stylette are withdrawn from the stomach. An intragastric balloon of this second type is described, for example, in UK Patent Application GB 2 090 747.

Even for the balloons of the second type, it may become desirable, from time-to-time, to add more saline in order to further expand the balloon to optimize weight control. In addition, one means of removing the balloon is to deflate it by removing the saline from the balloon through a tube before the empty balloon is removed from the stomach.

To accomplish the foregoing, intragastric balloons of the second type are normally equipped with a self-sealing valve into which the filler tube and or stylette can be inserted. One difficulty frequently encountered in this type of intragastric balloon is finding the valve when the balloon is already in the stomach and the surgeon is attempting to reinsert the filler tube for the purpose of adding or removing fluid from the balloon. Those experienced in the art will readily appreciate that manipulating the balloon while is situ to visually locate the valve is rather difficult, and the process of searching for the valve undesirably prolongs the procedure. Moreover, even after the filler valve has been visually located, it is often still difficult or awkward for the surgeon to reinsert the tube into the filler valve. This is because the balloon is slippery and positionally unstable. In other words, the usually spherical (or substantially spherical) intragastric balloons readily rotate in the stomach, so that even a slight disturbance of the balloon may place the filler valve into virtually any possible position relative to the filler tube poised to engage it.

Another problem associated with the heretofore known methods and devices is that following placement of the gastric balloons, a patient may experience nausea from the interaction of the recently placed gastric balloon with the stomach. This has been particularly noted when the gastric balloon is placed and filled to its capacity or substantially to its capacity in a single procedure.

Therefore, the present invention is directed at overcoming these problems associated with the prior art systems. These and other characteristics of the present invention will become apparent from the further disclosure to be made in the detailed description given below.

SUMMARY OF THE INVENTION

One aspect of the present invention is a gastric balloon including a shell, a receiver, and a retractable tubing housed in the receiver and extendable from the stomach of a patient to the mouth of the patient. The shell is inflated and deflated through the retractable tubing from outside the body of the patient.

Another aspect of the present invention is directed to a method of adding or removing fluid from an implanted gastric balloon by inserting a gastroscopic tool into the stomach of a patient and grasping an end of a retractable tubing housed in a receiver of the gastric balloon. Further steps of the method include withdrawing at least a portion of the retractable tubing from the stomach and out of the patient's mouth, and adding or removing fluid from the gastric balloon via the retractable tubing withdrawn from the patient.

Yet another aspect of the present invention is directed to a method of treating obesity. The method includes a step of implanting a gastric balloon including a shell, a receiver, and a retractable tubing housed in the receiver and extendable from the stomach of a patient to the mouth of the patient. The gastric balloon can be inflated and deflated through the retractable tubing from outside the body of the patient. A further step of the method entails inflating the gastric balloon to a first desired level to promote acclimatization of the gastric balloon in the stomach and to minimize nausea in the patient. Thereafter, the method entails a step of periodically increasing the inflation of the gastric balloon to subsequent desired levels known to minimize nausea and to achieve a continuous, regular, and safe rate of weight loss.

Further still, an aspect of the present invention is a method of implanting a gastric balloon including a step of providing a gastric balloon including a shell, a receiver, and a retractable tubing housed in the receiver and extendable from the stomach of a patient to the mouth of the patient. Further steps in the method include removing the retractable tubing from the receiver to minimize the volume of the uninflated gastric balloon, and gastroscopically implanting the gastric balloon in the stomach of a patient while maintaining at least a portion of the retractable tubing outside the mouth of the patient. Thereafter the method includes inflating the gastric balloon to a desired level, and releasing the retractable tubing to promote retraction of the retractable tubing into the stomach of the patient with or without endoscopic assistance.

Further characteristics, features, and advantages of the present invention will be apparent upon consideration of the following detailed description of the invention taken in conjunction with the following drawings, in which:

DETAILED DESCRIPTION OF THE PREFERRED EMBODIMENTS

Figure 1:
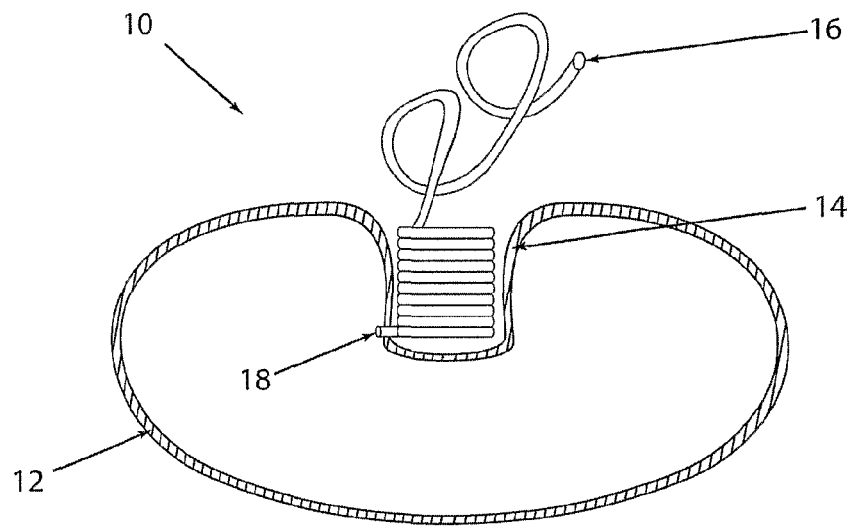
FIG. 1 is a cross-sectional view of a retractable tube gastric balloon according to one embodiment of the present invention.

The present invention is directed to a method and device for adjusting intragastric balloon volume in vivo or in situ, without removing the free-floating balloon from the stomach.

A gastric balloon 10 according to the present invention is shown in FIGS. 1-6. The gastric balloon 10 includes a shell 12, a retractable tubing 16, and a receiver 14 for housing the retractable tubing 16. In one embodiment of the present invention, the retractable tubing 16 has a memory that returns it to the receiver 18 after being withdrawn from the receiver 14 to an extended position for adding or removing fluid from the gastric balloon 10.

During implantation, an uninflated balloon 10 may be placed in the stomach with the tubing extended through the esophagus in order to minimize the size of the mass passing down the esophagus. Following initial placement, a desired quantity of fluid may be added to the gastric balloon 10 via the retractable tubing 16, a portion of which extents from the gastric balloon 10 through the esophagus and out of the patient's mouth. In some instances, despite the retractable nature of the retractable tubing 16, gastroscopic instrument assistance may also be required to properly stow the retractable tubing 16 in the receiver 14. Such steps may be necessary both after initial inflation or subsequent use of the gastric balloon 10 and the retractable tubing 16.

A method of adding or removing fluid from the gastric balloon 10 according to the present invention requires that a gastric balloon according to the present invention, such as those shown in FIGS. 1-6, be implanted in a patient. After implantation, inflating or deflating the gastric balloon 10 includes a step of accessing the retractable tubing 16 stowed on or in intragastric balloon 10. This accessing step is preferably performed gastroscopically. The retractable tubing 10, once accessed is grasped by a grasping tool (not shown), and a portion of the retractable tubing 10 is brought through the gastro-intestinal tract including the esophagus to the exterior of the patient via the mouth. Alternatively, the retractable tubing 10 could be brought through the nose of the patient without departing from the scope of the present invention. Next, using a syringe and needle or tubing with a shaped tip that is not injurious to the valve, fluid is added or removed through a self-sealing valve (not shown). The valve may be of a "Two Way Slit Valve" type described in commonly assigned international application number PCT US03/19414, the disclosure of which is incorporated herein by reference. Alternatively the valve could be a septum that is pierced by the needle or shaped tube tip, but resists flow of fluid out of the gastric balloon. The fluid enters the shell 12 of the gastric balloon 10 from the retractable tubing 16 through an interface 18. In some instances it may be desirable to include a valve at interface 18, or alternatively at both interface 18 and at an end of the retractable tubing 16 which is withdrawn from the patient to add or remove fluid.

Once a sufficient volume of liquid is added or removed from the gastric balloon, the retractable tubing 16 can be released. Upon release, the retractable tubing 16 will return from its extended position to its stowed position inside or on the gastric balloon 10 in receiver 14, which remains in the stomach of the patient.

The housing and accessing of the retractable tubing 16 in or on the gastric balloon 10 has many advantages over the devices and methods of the prior art. Initially, this allows for much more careful regulation and oversight in addressing a plateau in weight loss during the course of the balloon's implantation. This is enabled by the ease with which fluid can be added or removed from the gastric band 10. Previously, the addition of fluid was a time-consuming and challenging process that tended to dissuade a medical professional and the patient from undertaking these procedures unless deemed absolutely necessary.

In that same vein, the retractable tubing 16 allows for much easier deflation and removal of the gastric balloon 10 at the end of its implantation period. Because of the difficulty in deflating prior art gastric balloons, other methods of removal of the gastric balloons were developed, including piercing the balloon to drain the fluid contained therein into the stomach before removal of the remains endoscopically. Naturally, such a method requires the insertion of a piercing or cutting instrument into the body. As with the insertion of an inflation tube with the prior art devices, the substantially round gastric balloons have a tendency to move, and can be difficult to grasp by the grasping and piercing tool. By eliminating the need for any such device from entering the body, the potential for injury from inadvertently piercing the stomach during the removal process is greatly reduced.

Further, it has been determined that the incidence of nausea caused by the implantation of a gastric balloon can be greatly reduced by allowing the stomach to initially acclimatize itself to the gastric balloon when it is filled to a low volume in the recommended range. This volume can then be increased in stages after the patient is acclimatized to the device. Typically, this can be done over a period of weeks until a desired volume is reached.

With this acclimatization period comes yet another benefit in that the fear of overly rapid weight loss can be substantially eliminated. This enables the medical professional to closely monitor weight loss rates and alter the volume of the gastric balloon accordingly, preventing both the plateaus discussed above, and rapid weight loss which can have serious medical consequences. While some of the prior art devices could perform some of these similar functions, they could not be performed without substantial effort and time on the part of both the medical professional and the patient or serious inconvenience on the part of the patient.

Figure 2:
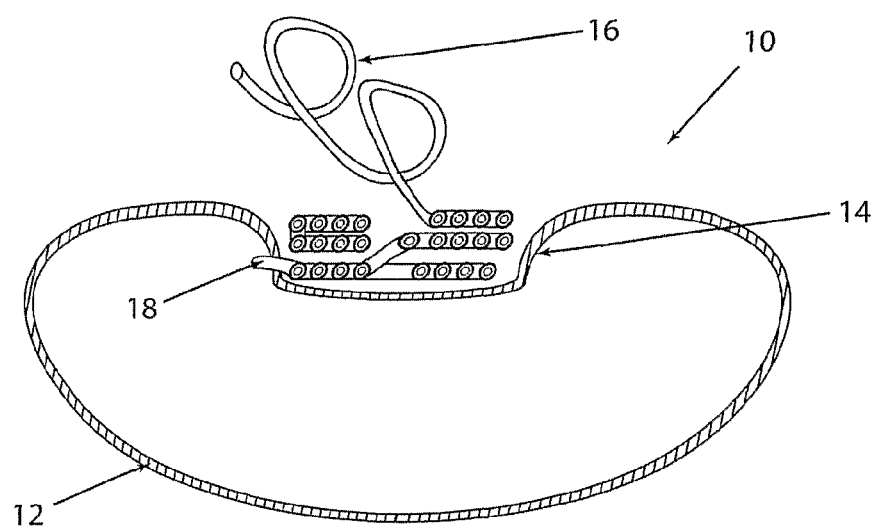
FIG. 2 is a cross-sectional view of a retractable tube gastric balloon according to a further embodiment of the present invention.
Figure 3:
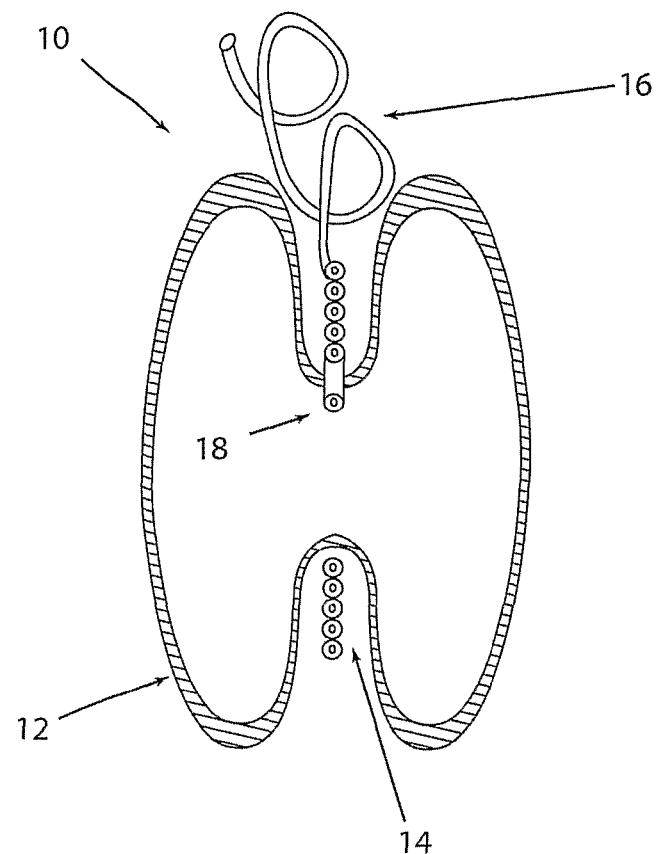
FIG. 3 is a cross-sectional view of a retractable tube gastric balloon according to another embodiment of the present invention.

In FIG. 1, the retractable tubing 16 is shown as a continuous coil. Various balloon shapes are required according to different tubing storage embodiments or receivers 14. Tubing stored in a coil requires a cylindrically shaped receiver 14 in the balloon surface as shown in FIG. 1. Tubing stored in a spiral, or stacks of spirals requires a shallower cylindrical recess or receiver 14 in the balloon 10 surface, as shown in FIG. 2. Another spiral configuration is that of a typical "yo-yo" toy, with the spiral beginning in a hemispherical groove receiver 14 and encircling the balloon multiple times and dividing the balloon into two hemispheres, as shown in FIG. 3. These combinations of retractable tubing 16 and receiver 14 are merely exemplary and other shapes and tubing arrangements are considered within the scope of the present invention.

The retractable tubing 16 may be soft and include a coil or radial spiral as a stiffener. Alternatively, semi-rigid tubing may be used that has been cured in a coil or spiral and has sufficient stiffness to return to this shape when released. In another embodiment, a superelastic shape memory alloy (SMA) may be used as a suitable coil spring to ensure that the retractable tubing 16 returns to the receiver 14 when not in use.

Figure 5:
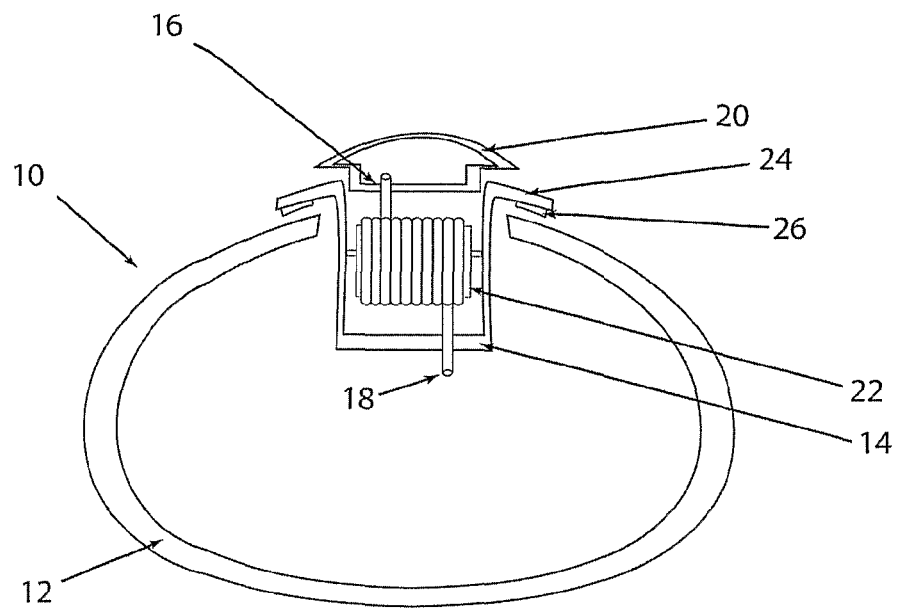
FIG. 5 is a cross-sectional view of a retractable tube gastric balloon according to yet another embodiment of the present invention.
Figure 6:
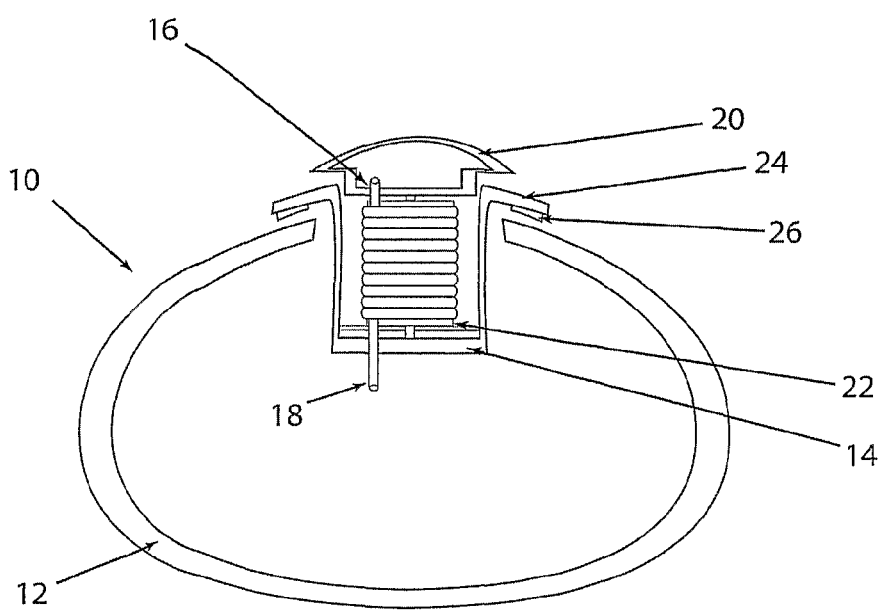
FIG. 6 is a cross-sectional view of a retractable tube gastric balloon according to the present invention.

Another configuration includes a torsionally loaded axle 22 that self-retracts the retractable tubing 16, as shown in FIGS. 5 and 6. The torsionally loaded axle 22 may be pre-grooved to assist in winding the retractable tubing 16 onto the axle 22 when released.

Figure 4:
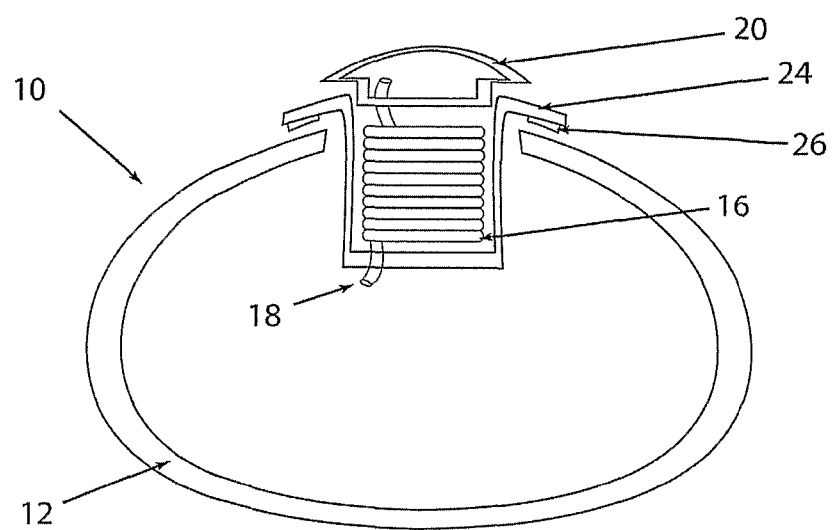
FIG. 4 is a cross-sectional view of a retractable tube gastric balloon according to the present invention.

Also shown in FIGS. 5 and 6 is a molded valve patch 24. In essence, the molded valve patch 24 is a receiver 14 formed separately from the shell 12. This molded valve patch 24 allows for separate construction and subsequent joining to the balloon shell 12. The molded valve patch 24 can have the retractable tubing 16 inserted and bonded to it prior to joining the shell 12. The shell 12 and the molded valve patch 24 may be joined together through a thermal or chemical bonding process. In some embodiments, this thermal or chemical bonding process may be performed in conjunction with an unvulcanized sheeting 26, as shown in FIGS. 4-6.

A further embodiment of the present invention includes a receiver cover or hood 20 to reduce the possibility of the retractable tubing 16 becoming entangled with stomach contents or deposition of stomach contents on the retractable tubing 16 or inside of the molded valve patch 24. This cover or cap 20 may be attached to the tubing and may have a feature to make it easily accessed by standard gastroscopic instrumentation. The cap 20 may also contain a valve or septum as discussed above or alternatively could simply act as a plug for the retractable tubing 16.

Although the invention has been particularly shown and described with reference to certain preferred embodiments, it will be readily appreciated by those of ordinary skill in the art that various changes and modifications may be made therein without departing from the spirit and scope of the invention.

We claim:

1. A gastric balloon comprising:
   a shell;
   a receiver dividing said shell substantially into two hemispheres and forming a small diameter portion of said shell;
   an interface on said small diameter portion of said shell to allow fluid to enter or exit said gastric balloon;
   a valve preventing the undesired addition or elimination of fluid from the gastric balloon; and
   a retractable tubing being movable between a stowed position in which said retractable tubing is housed on said small diameter portion of said receiver and an extended position in which said retractable tubing is withdrawn from said small diameter portion of said receiver and is extendable from a stomach of a patient to a mouth of the patient, said retractable tubing having one end coupled to said interface, and wherein said shell is inflated and deflated from outside a body of the patient via said retractable tubing.

2. The gastric balloon of claim 1 wherein said retractable tubing is housed on said small diameter portion of said receiver by being wrapped around said small diameter portion of said receiver.

3. The gastric balloon of claim 1 wherein said small diameter portion of said receiver is an indentation in said shell that extends entirely around said shell.

\* \* \* \* \*